(12) United States Patent
Aizawa et al.

(10) Patent No.: US 9,096,528 B2
(45) Date of Patent: Aug. 4, 2015

(54) 2-AMINONICOTINIC ACID ESTER DERIVATIVE AND BACTERICIDE CONTAINING SAME AS ACTIVE INGREDIENT

(71) Applicant: AGRO-KANESHO CO., LTD., Minato-ku (JP)

(72) Inventors: Ryo Aizawa, Tokorozawa (JP); Itaru Okada, Sagamihara (JP); Toshiki Fukuchi, Machida (JP); Masahiro Hatamoto, Oyama (JP)

(73) Assignee: AGRO-KANESHO CO., LTD., Minato-ku (JP)

( * ) Notice: Subject to any disclaimer, the term of this patent is extended or adjusted under 35 U.S.C. 154(b) by 0 days.

(21) Appl. No.: 14/412,130

(22) PCT Filed: Apr. 2, 2013

(86) PCT No.: PCT/JP2013/060061
§ 371 (c)(1),
(2) Date: Dec. 30, 2014

(87) PCT Pub. No.: WO2014/006945
PCT Pub. Date: Jan. 9, 2014

(65) Prior Publication Data
US 2015/0175551 A1 Jun. 25, 2015

(30) Foreign Application Priority Data
Jul. 4, 2012 (JP) ................. 2012-150421

(51) Int. Cl.
| | | |
|---|---|---|
| C07D 215/54 | (2006.01) | |
| C07D 213/80 | (2006.01) | |
| A01N 43/40 | (2006.01) | |
| C07D 221/04 | (2006.01) | |
| A01N 43/42 | (2006.01) | |

(52) U.S. Cl.
CPC .............. *C07D 221/04* (2013.01); *A01N 43/40* (2013.01); *A01N 43/42* (2013.01); *C07D 213/80* (2013.01); *C07D 215/54* (2013.01)

(58) Field of Classification Search
None
See application file for complete search history.

(56) References Cited

U.S. PATENT DOCUMENTS

| 5,877,177 | A | 3/1999 | Taveras |
| 5,968,875 | A | 10/1999 | Bis et al. |
| 2002/0016345 | A1 | 2/2002 | Edmunds et al. |
| 2004/0038972 | A1 | 2/2004 | Den Hartog et al. |
| 2006/0063820 | A1 | 3/2006 | Renold et al. |
| 2008/0247964 | A1 | 10/2008 | Xu et al. |
| 2010/0063063 | A1 | 3/2010 | Benbow et al. |
| 2010/0168175 | A1 | 7/2010 | Adelt et al. |
| 2010/0298314 | A1 | 11/2010 | Reddy et al. |
| 2011/0009454 | A1 | 1/2011 | Matsuzaki et al. |
| 2011/0190267 | A1 | 8/2011 | Franklin et al. |
| 2011/0230445 | A1 | 9/2011 | Benbow et al. |
| 2012/0225910 | A1 | 9/2012 | Pfefferkorn et al. |
| 2013/0165452 | A1 | 6/2013 | Benbow et al. |

FOREIGN PATENT DOCUMENTS

| EP | 0 650 961 | 5/1995 |
| JP | 9 249648 | 9/1997 |
| JP | 10 72440 | 3/1998 |

(Continued)

OTHER PUBLICATIONS

Sergio H. Szajnman, et al., "Design and Synthesis of Aryloxyethyl Thiocyanate Derivatives as Potent Inhibitors of *Trypanosoma cruzi* Proliferation", J. Med. Chem., vol. 43, pp. 1826-1840, (2000).
International Search Report Issued Jul. 9, 2013 in PCT/JP13/060061 Filed Apr. 2, 2013.

*Primary Examiner* — Zinna Northington Davis
(74) *Attorney, Agent, or Firm* — Oblon, McClelland, Maier & Neustadt, L.L.P.

(57) ABSTRACT

The present invention provides a bactericide containing a 2-aminonicotinic acid ester derivative as an active ingredient. The active ingredient is represented by the following formula [I]:

$$\text{[I]}$$

(wherein, $R^1$ represents a hydrogen atom or a $C_1$-$C_4$ alkyl group, $R^2$ represents a hydrogen atom or a $C_1$-$C_4$ alkyl group, $R^1$ and $R^2$ may be combined together to form an alkylene chain, $R^3$ represents a hydrogen atom or a $C_1$-$C_4$ alkyl group, $R^4$ represents a hydrogen atom, a cyano group or a $C_1$-$C_4$ alkyl group, $R^5$ and $R^6$ independently represent a hydrogen atom, a halogen atom, a $C_1$-$C_4$ alkyl group, a $C_1$-$C_4$ alkoxy group, a $C_1$-$C_4$ alkylthio group, a $C_1$-$C_4$ alkylsulfinyl group, a $C_1$-$C_4$ alkylsulfonyl group, a nitro group, a cyano group, a $C_1$-$C_4$ haloalkyl group, a $C_1$-$C_4$ haloalkoxy group or a $C_1$-$C_4$ haloalkylthio group, A and B independently represent a methine (CH) group or a nitrogen atom).

2 Claims, No Drawings

(56) References Cited

FOREIGN PATENT DOCUMENTS

| | | |
|---|---|---|
| JP | 2004 51628 | 2/2004 |
| JP | 2010 83861 | 4/2010 |
| WO | 94 29267 | 12/1994 |
| WO | 98 33772 | 8/1998 |
| WO | 98 57946 | 12/1998 |
| WO | 00 15615 | 3/2000 |
| WO | 02 02515 | 1/2002 |
| WO | 03 101980 | 12/2003 |
| WO | 2004 056735 | 7/2004 |
| WO | 2005 068430 | 7/2005 |
| WO | 2007 133561 | 11/2007 |
| WO | 2008 082490 | 7/2008 |
| WO | 2010 029461 | 3/2010 |
| WO | 2011 083304 | 7/2011 |

2-AMINONICOTINIC ACID ESTER DERIVATIVE AND BACTERICIDE CONTAINING SAME AS ACTIVE INGREDIENT

CONTINUING DATA

This application is a 371 of PCT/JP2013/060061 filed Apr. 2, 2013.

TECHNICAL FIELD

The present invention relates to a 2-aminonicotinic acid ester derivative and a bactericide containing the same as an active ingredient.

BACKGROUND ART

In a field of agriculture and horticulture, various bactericides aiming at controlling a wide variety of pathogenic bacteria have been developed and practically used.

However, commonly used conventional agricultural chemicals do not necessarily satisfy requirements of their effects, spectrum, residual activities and the like as well as those of reducing application frequencies, application doses and the like. In addition, there is a problem of the occurrence of pathogenic bacteria which have developed resistance to commonly used conventional agricultural chemicals. For example, in cultivating vegetables, fruit trees, flowering plants, tea plants, barleys or wheats, rice plants and the like, for example, various pathogenic bacteria having developed resistance to various types of bactericides, such as triazole, imidazole, pyrimidine, benzimidazole, dicarboximide, phenylamide, strobilurin bactericides and the like have occurred in various regions, and the control of these resistant pathogenic bacteria becomes increasingly difficult year by year. Accordingly, the development of a novel agricultural chemical, which exhibits a sufficient control effect on a wide variety of pathogenic bacteria having developed resistance to commonly used conventional bactericides for use in agriculture and horticulture even at a low dose, and which has lower adverse influence on environment, has been continuously demanded.

In order to meet these demands, various new bactericides have been proposed, but they do not necessarily satisfy the above-described demands.

Patent Document 1 discloses a carboxamide derivative having a bactericidal activity and having the following structure. However, the compound disclosed in Patent Document 1 has a carboxamide bond at position 3 of the pyridine ring, but does not have an ester bond.

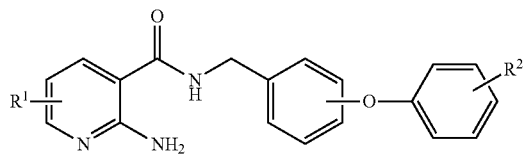

(Patent Document 1)

Patent Document 2 discloses the following ester derivative having an amino group at position 2 of the pyridine ring as a reaction intermediate (page 265, Example 35, Compound No. 757). However, this compound has a methoxy group, but not a phenoxy group. Further, this compound is disclosed merely as an intermediate in the production of a pharmaceutically active compound disclosed in Patent Document 2, and Patent Document 2 does not disclose a bactericidal activity.

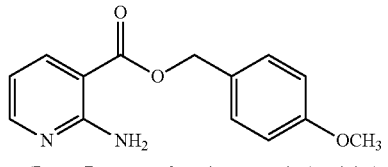

(Patent Document 2, a pharmaceutical activity)

Patent Document 3-6 disclose, as specifically synthesized compounds, ester derivatives which do not have an amino group at position 2 of the pyridine ring as follows. As their representative examples, the following compounds are exemplified. It is disclosed that these compounds have insecticidal or herbicidal activities, but it is not disclosed at all that these compounds have any bactericidal activity.

Patent Document 3 discloses the following compound (page 43, Compound No. 1.59). However, Patent Document 3 relates to use as an insecticide, but does not disclose a compound having an amino group at position 2 of the pyridine ring.

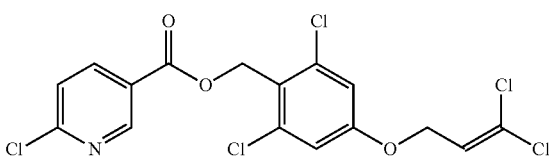

(Patent Document 3, an insecticidal activity)

Patent Document 4 discloses the following compound (page 33, Compounds 270 and 271). However, Patent Document 4 relates to use as an insecticide, but does not disclose a compound having an amino group at position 2 of the pyridine ring.

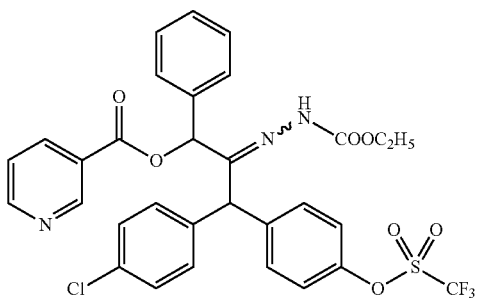

(Patent Document 4, an insecticidal activity)

Patent Document 5 discloses the following compound (page 78, Compound No. 1.3717). However, Patent Document 5 relates to use as a herbicide, but does not disclose a compound having an amino group at position 2 of the pyridine ring.

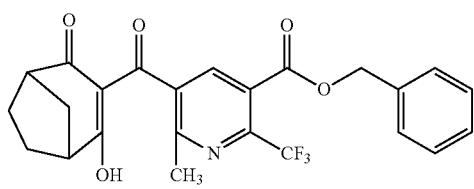

(Patent Document 5, a herbicidal activity)

Patent Document 6 discloses the following compound (page 42, Compound No. 229). However, Patent Document 6 relates to use as a herbicide, but does not disclose a compound having an amino group at position 2 of the pyridine ring.

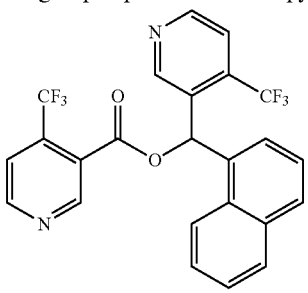

(Patent Document 6, a herbicidal activity)

Further, Patent Document 7 or Patent Document 8 discloses, as specific compounds endowed with bactericidal activities, the following compounds.

Specifically, Patent Document 7 discloses the following compound (page 50, Compound No. 48). However, Patent Document 7 does not disclose a compound having an amino group at position 2 in the pyridine ring.

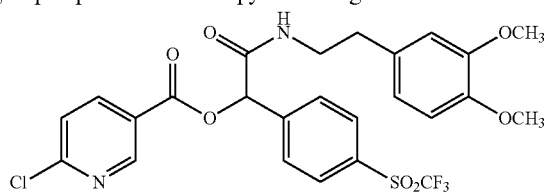

(Patent Document 7, a bactericidal activity)

Further, Patent Document 8 discloses the following compound (page 40, Compound Number 22). However, Patent Document 8 does not disclose a compound having an amino group at position 2 of the pyridine ring.

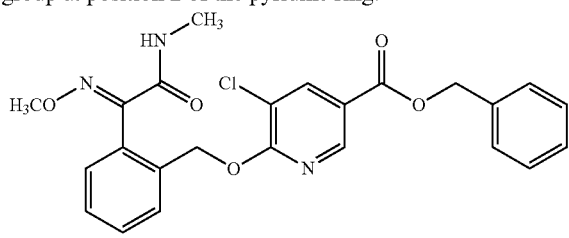

(Patent Document 8, a bactericidal activity)

On the other hand, Patent Document 9-14 specifically discloses the following compounds endowed with pharmaceutical activities. In detail, Patent Document 9 discloses the following compound (page 42, Example 186). However, Patent Document 9 does not disclose a compound having an amino group at position 2 of the pyridine ring. In addition, the compound of Patent Document 9 is only disclosed as a pharmaceutically active substance.

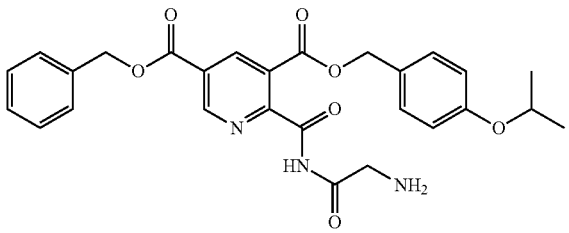

(Patent Document 9, a pharmaceutical activity)

Furthermore, Patent Document 10 specifically discloses the following compound (page 32, the right compound in the reaction scheme of step 3). However, this compound is merely disclosed as a reaction intermediate, and Patent Document 10 does not disclose a compound having an amino group at position 2 of the pyridine ring.

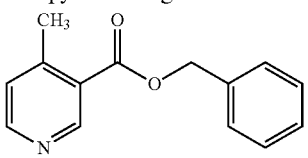

(Patent Document 10, a pharmaceutical activity)

Patent Document 11 discloses the following compound as a pro-3-nicotinoyl (page 17). However, Patent Document 11 does not disclose a compound having an amino group at position 2 of the pyridine ring. In addition, the compound of Patent Document 11 is merely disclosed as a pharmaceutically active substance.

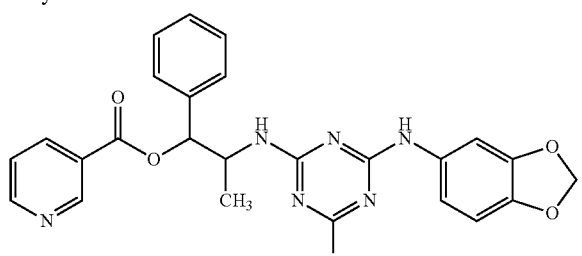

(Patent Document 11, a pharmaceutical activity)

Patent Document 12 discloses the following compound (page 51, E step 1). However, Patent Document 11 discloses this compound only as an intermediate, but does not disclose a compound having an amino group at position 2 of the pyridine ring. Additionally, the compound of Patent Document 11 is merely disclosed as a pharmaceutically active substance.

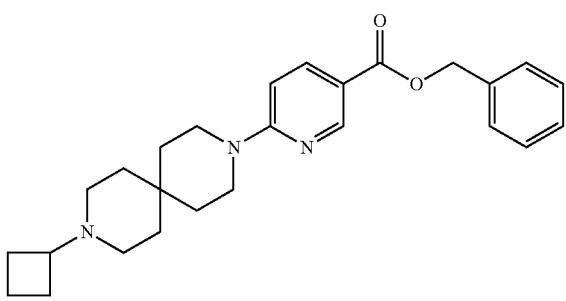

(Patent Document 12, a pharmaceutical activity)

Patent Document 13 discloses the following compound (page 56 (I-17b)). However, Patent Document 13 does not disclose a compound having an amino group at position 2 of the pyridine ring. In addition, the compound of Patent Document 13 is merely disclosed as a pharmaceutically active substance.

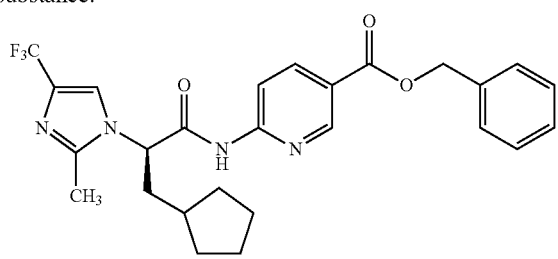

(Patent Document 13, a pharmaceutical activity)

Patent Document 13 discloses the following compound (page 93, the synthesis scheme). However, Patent Document 13 discloses this compound only as an intermediate, but does not disclose a compound having an amino group at position 2 of the pyridine ring. Additionally, the compound of Patent Document 13 is merely disclosed as a pharmaceutically active substance.

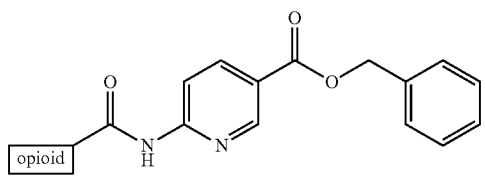

(Patent Document 14, a pharmaceutical activity)

Non-Patent Document 1 relates to a pharmaceutically active compound which is used as a therapeutic agent for Chagas disease. Non-Patent Document 1 discloses a pharmaceutically active compound having a phenoxybenzyloxy backbone. However, Non-Patent Document 1 does not disclose a compound having this backbone into which 2-aminonicotinic acid is introduced.

PRIOR ART DOCUMENTS

Patent Document

Patent Document 1: JP-A-2010-083861
Patent Document 2: WO2008/082490
Patent Document 3: WO2004/056735
Patent Document 4: WO2002/002515
Patent Document 5: WO2000/015615
Patent Document 6: JP-A-2004-051628
Patent Document 7: WO1994/029267
Patent Document 8: WO1998/033772
Patent Document 9: EP1995-650961
Patent Document 10: WO1998/057946
Patent Document 11: WO2003/101980
Patent Document 12: WO2007/133561
Patent Document 13: WO2010/029461
Patent Document 14: WO2011/083304

Non-Patent Document

Non-Patent Document 1: Journal of Medicinal Chemistry, Vol. 43, page 1826 (2000)

SUMMARY OF INVENTION

Problem to be Solved

The present invention is to provide a novel compound useful for controlling a wide variety of bacteria, and, in particular, to provide a compound which exhibits a high control effect on a wide variety of bacteria which show tolerance to conventional bactericides, as well as to provide a compound which also exhibits the effect at a low dose, and therefore, has a high safety with fewer problems such as residual toxicity, environmental pollution and the like.

Means for Solving the Problem

The present inventors have conducted intensive studies in order to solve the above problem, and as a result, have found that the 2-aminonicotinic acid ester derivative defined by the following formula exhibit the properties which can satisfy the above demands, and thus completed the present invention.

That is, the present invention relates to a 2-aminonicotinic acid ester derivative represented by the following formula [I]:

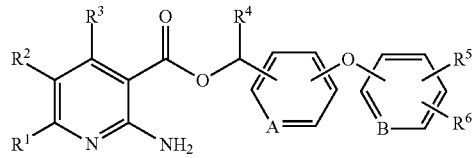

(wherein:

$R^1$ represents a hydrogen atom or a $C_1$-$C_4$ alkyl group, $R^2$ represents a hydrogen atom, a $C_1$-$C_4$ alkyl group, or $R^1$ and $R^2$ are combined together to form the following group:

or

, $R^3$ represents a hydrogen atom or a $C_1$-$C_4$ alkyl group, $R^4$ represents a hydrogen atom, a cyano group or a $C_1$-$C_4$ alkyl group, $R^5$ and $R^6$ independently represent a hydrogen atom, a halogen atom, a $C_1$-$C_4$ alkyl group, a $C_1$-$C_4$ alkoxy group, a $C_1$-$C_4$ alkylthio group, a $C_1$-$C_4$ alkylsulfinyl group, a $C_1$-$C_4$ alkylsulfonyl group, a nitro group, a cyano group, a $C_1$-$C_4$ haloalkyl group, a $C_1$-$C_4$ haloalkoxy group or a $C_1$-$C_4$ haloalkylthio group, A and B independently represent a methine (CH) group or a nitrogen atom) (hereinafter also referred to as "the present compound"), as well as a bactericide comprising the same as an active ingredient.

Effects by the Invention

The present compound exhibits an excellent effect on a wide variety of bacteria.

EMBODIMENTS FOR CARRYING OUT THE INVENTION

Hereinafter, the present invention will be described more in detail.

In the present compound represented by the formula [I], the $C_1$-$C_4$ alkyl groups represented by $R^1$, $R^2$, $R^3$, $R^5$ and $R^6$ include, for example, a methyl group, an ethyl group, an n-propyl group, an isopropyl group, an n-butyl group, an isobutyl group, a sec-butyl group, a tert-butyl group and the like. The halogen atoms represented by $R^5$ and $R^6$ include, for example, a fluorine atom, a chlorine atom, a bromine atom and an iodine atom.

The $C_1$-$C_4$ alkoxy groups represented by $R^5$ and $R^6$ include, for example, a methoxy group, an ethoxy group, an n-propoxy group, an isopropoxy group, an n-butoxy group, an isobutoxy group, a sec-butoxy group and a tert-butoxy group.

The $C_1$-$C_4$ alkylthio groups represented by $R^5$ and $R^6$ include, for example, a methylthio group, an ethylthio group, an n-propylthio group, an isopropylthio group, an n-butylthio group, an isobutylthio group, a sec-butylthio group, and a tert-butylthio group.

The $C_1$-$C_4$ alkylsulfinyl groups represented by $R^5$ and $R^6$ include, for example, a methylsulfinyl group, an ethylsulfinyl group, an n-propylsulfinyl group, an isopropylsulfinyl group, an n-butylsulfinyl group, an isobutylsulfinyl group, a sec-butylsulfinyl group, and a tert-butylsulfinyl group.

The $C_1$-$C_4$ alkylsulfonyl groups represented by $R^5$ and $R^6$ include, for example, a methylsulfonyl group, an ethylsulfonyl group, an n-propylsulfonyl group, an isopropylsulfonyl group, an n-butylsulfonyl group, an isobutylsulfonyl group, a sec-butylsulfonyl group and a tert-butylsulfonyl group.

The $C_1$-$C_4$ haloalkyl groups represented by $R^5$ and $R^6$ include, for example, a monofluoromethyl group, a difluoromethyl group, a trifluoromethyl group, a monochloromethyl group, a dichloromethyl group, a trichloromethyl group, a monobromomethyl group, a dibromomethyl group, a tribromomethyl group, a 1-fluoroethyl group, a 2-fluoroethyl group, a 2,2-difluoroethyl group, a 2,2,2-trifluoroethyl group, a 2-chloro-2,2-difluoroethyl group, a 1-chloroethyl group, a 2-chloroethyl group, a 2,2,-dichloroethyl group, a 2,2,2-trichloroethyl group, a 1-bromoethyl group, a 2-bromoethyl group, a 2,2-dibromoethyl group, a 2,2,2-tribromoethyl group, a 2-iodoethyl group, a pentafluoroethyl group, a 3-fluoropropyl group, a 3-chloropropyl group, a 3-bromopropyl group, a 1,3-difluoro-2-propyl group, a 3,3,3-trifluoropropyl group, a 1,3-dichloro-2-propyl group, a 1,1,1-trifluoro-2-propyl group, a 1-chloro-3-fluoro-2-propyl group, a 1,1,1,3,3,3-hexafluoro-2-propyl group, a 1,1,1,3,3,3-hexafluoro-2-chloro-2-propyl group, a 2,2,3,3,3-pentafluoropropyl group, a heptafluoroisopropyl group, a heptafluoro-n-propyl group, a 4-fluorobutyl group, a 4,4,4-trifluorobutyl group, a nonafluoro-n-butyl group, and a nonafluoro-2-butyl group.

The $C_1$-$C_4$ haloalkoxy groups represented by $R^5$ and $R^6$ include, for example, a monofluoromethoxy group, a difluoromethoxy group, a trifluoromethoxy group, a monochloromethoxy group, a dichloromethoxy group, a trichloromethoxy group, a monobromomethoxy group, a dibromomethoxy group, a tribromomethoxy group, a 1-fluoroethoxy group, a 2-fluoroethoxy group, a 2,2-difluoroethoxy group, a 2,2,2-trifluoroethoxy group, a 2-chloro-2,2-difluoroethoxy group, a 1-chloroethoxy group, a 2-chloroethoxy group, a 2,2,-dichloroethoxy group, a 2,2,2-trichloroethoxy group, a 1-bromoethoxy group, a 2-bromoethoxy group, a 2,2-dibromoethoxy group, a 2,2,2-tribromoethoxy group, a 2-iodoethoxy group, a pentafluoroethoxy group, a 3-fluoropropoxy group, a 3-chloropropoxy group, a 3-bromopropoxy group, a 1,3-difluoro-2-propoxy group, a 3,3,3-trifluoropropoxy group, a 1,3-dichloro-2-propoxy group, a 1,1,1-trifluoro-2-propoxy group, a 1-chloro-3-fluoro-2-propoxy group, a 1,1,1,3,3,3-hexafluoro-2-propoxy group, a 1,1,1,3,3,3-hexafluoro-2-chloro-2-propoxy group, a 2,2,3,3,3-pentafluoropropoxy group, a heptafluoroisopropoxy group, a heptafluoro-n-propoxy group, a 4-fluorobutoxy group, a 4,4,4-trifluorobutoxy group, a nonafluoro-n-butoxy group, and a nonafluoro-2-butoxy group.

The haloalkylthio groups represented by $R^5$ and $R^6$ include, for example, a monofluoromethylthio group, a difluoromethylthio group, a trifluoromethylthio group, a monochloromethylthio group, a dichloromethylthio group, a trichloromethylthio group, a monobromomethylthio group, a dibromomethylthio group, a tribromomethylthio group, a 1-fluoroethylthio group, a 2-fluoroethylthio group, a 2,2-difluoroethylthio group, a 2,2,2-trifluoroethylthio group, a 2-chloro-2,2-difluoroethylthio group, a 1-chloroethylthio group, a 2-chloroethylthio group, a 2,2,-dichloroethylthio group, a 2,2,2-trichloroethylthio group, a 1-bromoethylthio group, a 2-bromoethylthio group, a 2,2-dibromoethylthio group, a 2,2,2-tribromoethylthio group, a 2-iodoethylthio group, a pentafluoroethylthio group, a 3-fluoropropylthio group, a 3-chloropropylthio group, a 3-bromopropylthio group, a 1,3-difluoro-2-propylthio group, a 3,3,3-trifluoropropylthio group, a 1,3-dichloro-2-propylthio group, a 1,1,1-trifluoro-2-propylthio group, a 1-chloro-3-fluoro-2-propylthio group, a 1,1,1,3,3,3-hexafluoro-2-propylthio group, a 1,1,1,3,3,3-hexafluoro-2-chloro-2-propylthio group, a 2,2,3,3,3-pentafluoropropylthio group, a heptafluoroisopropylthio group, a heptafluoro-n-propylthio group, a 4-fluorobutylthio group, a 4,4,4-trifluorobutylthio group, a nonafluoro-n-butylthio group, and a nonafluoro-2-butylthio group.

Further, $R^4$ represents a hydrogen atom, a cyano group or a $C_1$-$C_4$ alkyl group, and examples of the $C_1$-$C_4$ alkyl groups include alkyl groups represented by $R^1$, $R^2$, $R^3$, $R^5$ and $R^6$.

The present compound is a novel compound which has not been disclosed in any prior art documents and can be produced, for example, according to the following reaction scheme from known starting compounds.

Reaction scheme

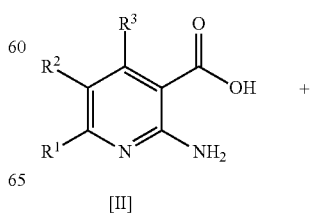

[II]

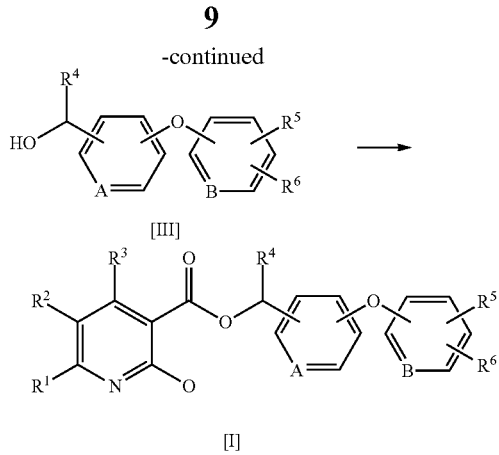

(wherein, $R^1$, $R^2$, $R^3$, $R^4$, $R^5$, $R^6$, A and B are the same as defined in the above formula [I]).

The 2-aminonicotinic acid ester derivative represented by the general formula [I] of the present invention can be produced by reacting the 2-aminonicotinic acid derivative represented by the general formula [II] with the alcohol derivative represented by the general formula [III] in an inert solvent in the presence of a condensing agent and a base.

The compounds [II] and [III] here are already known compounds or compounds which can be readily synthesized from known compounds by those skilled in the art.

The reaction is conducted at a reaction temperature in the range normally of −20° C.-120° C., preferably of 0° C.-40° C., for a reaction time in the range normally of 0.2 hour-24 hours, preferably of 1 hour-5 hours. The phenoxybenzylalcohol derivative represented by the general formula [III] is used in the range normally of 1-5 times by mole, preferably of 1-1.5 times by mole per the 2-aminonicotinic acid derivative represented by the general formula [II].

Examples of the condensing agents used in the reaction include, for example, diethyl phosphorocyanidate (DEPC), carbonyldiimidazole (CDI), 1,3-dicyclohexylcarbodiimide (DCC), 1-ethyl-3-(3-dimethylaminopropyl) carbodiimide hydrochloride, chloroformates, 2-chloro-1-methylpyridinium iodide and the like, and the amount of the condensing agent used is in the range normally of 1-3 times by mole, preferably of 1-1.5 times by mole per the 2-aminonicotinic acid derivative represented by the general formula [II].

The bases include, for example, inorganic bases such as sodium hydroxide, potassium hydroxide, sodium carbonate, potassium carbonate, sodium bicarbonate and potassium bicarbonate; acetates such as sodium acetate and potassium acetate; metal alkoxides such as potassium t-butoxide, sodium methoxide, sodium ethoxide; tertiary amines such as triethylamine, diisopropylethylamine and 1,8-diazabicyclo[5,4,0]undec-7-ene; nitrogen-containing aromatic compounds such as pyridine, dimethylaminopyridine and the like. The amount of the base used is in the range normally of 1-10 times by mole, preferably of 1-2 times by mole per one mole of the 2-aminonicotinic acid derivative represented by the general formula [II].

A solvent may or may not be used in the reaction, but if a solvent is used, the solvent is not particularly limited as long as it does not significantly inhibit the reaction. A wide variety of solvents may be used and suitable examples. The solvents to be used include, for example, chain or cyclic ethers such as dimethyl ether, diethyl ether, diisopropyl ether, dibutyl ether, tetrahydrofuran and dioxane; aromatic hydrocarbons such as benzene, toluene and xylene; halogenated hydrocarbons such as methylene chloride, chloroform and carbon tetrachloride; nitriles such as acetonitrile; esters such as methyl acetate, ethyl acetate and butyl acetate; polar solvents such as N,N-dimethylformamide, N,N-dimethylacetamide, dimethylsulfoxide, 1,3-dimethyl-2-imidazolidinone; and the like. These inert solvents may be used alone or in a mixture of them.

After the reaction, the objective compound can be easily isolated from the reaction system containing it by a conventional method. The objective compound can be prepared by purifying it by, for example, recrystallization, column chromatography and the like.

The 2-aminonicotinic acid derivative represented by the general formula [II] used for the reaction can be readily synthesized from a known compound, for example, according to the method described in JP-A-2010-083861 (Patent Document 1).

The alcohol derivative represented by the general formula [III] used for the reaction can be readily synthesized from a known compound, for example, according to the method described in Journal of Medicinal Chemistry, Vol. 43, page 1826 (2000) (Non Patent Document 1).

The present compound can be used for controlling diseases of, fruit trees, for example, an avocado tree, an apricot tree, a fig tree, an iyokan orange tree, an ume tree, a satsuma mandarin orange tree, a cherry tree, a persimmon tree, a kabosu tree, a kiwi tree, a plum tree, a pear tree, a tankan mandarin orange tree, a dekopon mandarin orange tree, an Asian pear tree, a summer orange tree, a nectarine tree, a hassaku orange tree, a papaya tree, a loquat tree, a grape tree, a shaddock tree, a mango tree, a peach tree, a citron tree, an apple tree, a lemon tree and the like: grains, for example, a barley, a wheat, a paddy rice, a maize, an adlay, a rye, "Okabo" (rice grown in dry field) and the like; potatoes, for example, a sweet potato, a potato, a taro, a yam and the like; vegetables, for example, an adzuki bean, a strawberry, a kidney bean, a pea, a gumbo, a turnip, a pumpkin, a cabbage, a cucumber, a burdock, a cowpea, a pickling melon, a watermelon, a celery, a broad bean, a radish, a soybean, an onion, a sugar beet, a pepper, a wax gourd, a tomato, an eggplant, a bitter melon, a carrot, a leek, a Chinese cabbage, a parsley, a bell pepper, a sponge cucumber, a melon, a lettuce and the like; industrial crops, for example, a sugarcane, a turf, a tobacco, a tea, a rapeseed, a hop and the like; flowering plants, for example, a hydrangea, a carnation, a gerbera, a gazania, a chrysanthemum, a snapdragon, a calendula, a salvia, a perennial soaproot, a sweet pea, a statice, a saintpaulia, a dahlia, a timothy, a delphinium, a prairie gentian, a verbena, a sunflower, roses, a begonia, a petunia, a poinsettia, a lilac, a gentian, a rosemary and the like; trees, for example, acacias, a maple, evergreen oaks, a katsura, a paulownia, a keyaki, cherry trees, chinkapins, azaleas, camellias, oaks, alders, and willows.

Diseases to be treated include phytopathogenic fungi, bacteria and actinomycetes, and specifically include, *Pyricularia oryzae, Cochliobolus miyabeanus, Rhizoctonia solani, Burkholderia glumae, Xanthomonas oryzae* pv. *oryzae, Acidovorax avenae* subsp. *avenae, Erinia ananas, Pseudomonas fuscovaginae, Burkholderia plantarii* and the like of a rice plant; *Erysiphe graminis, Gibberella zeae, Puccinia striiformis, P. graminis, P. recondita, P. hordei, Typhula* sp., *Micronectriella nivalis, Ustilago tritici, U. nuda, Tilletia caries, Pseudocercosporella herpotrichoides, Rhynchosporium secalis, Septoria tritici, Leptosphaeria nodorum, Pyrenophora teres,*

*Helminthosporium zonatum* Ikata, *Pseudomonas syringae* pv. *japonica* and the like of barleys or wheats; *Diaporthe citri, Elsinoe fawcetti, Penicillium digitatum, P. italicum, Phytophthora citrophthora, P. nicotianae, Phyllosticta citricarpa,*

*Xanthomonas campestris* pv. *citri* and the like of citruses; *Monilinia mali, Valsa mali, Podosphaera leucotricha, Alternaria mali, Venturia inaequalis, Mycospherella pomi, Colletotrichum acutatum, Botryosphaeria berengeriana, Gymnosporangium yamadae, Monilinia fructicola* and the like of an apple tree; *Venturia nashicola, V. pirina, Alternaria kikuchiana, Gymnosporangium haraeanum, Monilinia fructigena* and the like of an Asian pear tree; *Monilinia fructicola, Cladosporium carpophilum,*
*Phomopsis* sp., *Xanthomonas campestris* pv. *pruni* and the like of a peach tree; *Elsinoe ampelina, Colletotrichum acutatum, Uncinula necator, Phakopsora ampelopsidis, Guignardia bidwellii, Plasmopara viticola, Monilinia fructigena, Cladosporium viticolum, Agrobacterium vitis* and the like of a grape tree; *Gloeosporium kaki, Cercospora kaki, Mycoshaerella nawae* and the like a persimmon tree;
*Cercospora kikuchii, Elsinoe glycines, Diaporthe phaseolorum* var. *sojae, Pseudomonas savastanoi* pv. *glycinea, Xanthomonas campestris* pv. *glycines* and the like of a soybean; *Colletotrichum lindemthianum, Pseudomonas savastanoi* pv. *phaseolicola, Xanthomonas campestris* pv. *phaseoli* and the like of a kidney bean; *Cercospora personata, Cercospora arachidicola* and the like of a peanut; *Erysiphe pisi* and the like of a pea; *Colletotrichum lagenarium, Sphaerotheca fuliginea, Oidiopsis taurica, Didymella bryoniae, Fusarium oxysporum, Pseudoperonospora cubensis, Phytophthora* sp., *Pythium* sp., *Pseudomonas syringae* pv. *lachrymans, Xanthomonas campestris* pv. *cucuribitae* and the like of melons; *Alternaria solani, Cladosporium fulvum, Phytophthora infestans, Ralstonia solanacearum,*
*Clavibacter michiganense* subsp. *michiganense, Pseudomonas corrugata, Erwinia carotovora* subsp. *carotovora* and the like of a tomato; *Phomopsis vexans, Erysiphe cichoracearum, Ralstonia solanacearum* and the like of an eggplant; *Alternaria japonica, Cercosporella brassicae, Xanthomonas campestris* pv. *campestris, Erwinia carotovora* subsp. *carotovora, Pseudomonas syringae* pv. *marginalis* and the like of vegetables of the family Cruciferae; *Puccinia allii* and the like of a leek; *Alternaria solani, Phytophthora infestans, Rhizoctonia solani, Erwinia carotovora* subsp. *carotovora, Erwinia carotovora* subsp. *atroseptica, Ralstonia solanacearum, Streptomyces scabies, Streptomyces acidiscabies* and the like of a potato; *Sphaerotheca humuli, Ralstonia solanacearum, Pseudomonas marginalis* pv. *marginalis, Xanthomonas campestris, Xanthomonas fragariae* and the like of a strawberry; *Exobasidium reticulatum, Elsinoe leucospila, Pseudomonas syringae* pv. *theae, Ralstonia solanacearum, Xanthomonas campestris* pv. *theicola* and the like of a tea plant;
*Alternaria longipes, Erysiphe cichoracearum, Colletotrichum tabacum, Peronospora tabacina, Phytophthora nicotianae, Erwinia carotovora* subsp. *carotovora* and the like of a tobacco; *Cercospora beticola, Aphanomyces cochliodes* and the like of a sugar beet; *Alternaria dauci, Rhizobacter dauci, Streptomyces scabies* of a carrot; *Diplocarpon rosae, Sphaerotheca pannosa, Agrobacterium tumefaciens* and the like of a rose; *Septoria chrysanthemi-indici, Puccinia horiana, Agrobacterium tumefaciens* and the like of a chrysanthemum; *Botrytis cinerea, Sclerotinia sclerotiorum* and the like of various crops, but diseases are not limited to the bacteria described herein.

The present compound can be used in a wide variety of formulations. In order to prepare these formulations, a wide variety of pesticide adjuvants conventionally used in the technical field of bactericides for agriculture and horticulture can be appropriately used. The formulations of bactericides for agriculture and horticulture include, for example, an emulsifiable concentrate, a wettable powder, a water dispersible granule, a water soluble powder, a soluble concentrate, a dustable powder, a suspension concentrate (flowable), a dry flowable, a fine granule, a granule, a tablet, an oil solution, a propellant, an aerosol and the like. Of course, one or more present compounds can be combined as an active ingredient.

Such pesticide adjuvants can be used for the purposes, for example, of improving effects of bactericides for agriculture and horticulture, of improving stability and dispersibility and the like. The pesticide adjuvants include, for example, a carrier (a diluent), a spreader, an emulsifier, a wetter-spreader, a dispersant, a disintegrator and the like. The liquid carriers include, water, aromatic hydrocarbons such as toluene and xylene, alcohols such as methanol, butanol and glycol, ketones such as acetone, amides such as dimethylformamide, sulfoxides such as dimethylsulfoxide, methylnaphthalene, cyclohexane, animal and vegetable oils, fatty acids and the like. In addition, the solid carriers include, clay, kaolin, talc, diatomite, silica, calcium carbonate, montmorillonite, bentonite, feldspar, quartz, alumina, sawdust, nitrocellulose, starch, gum arabic and the like.

As an emulsifier and a dispersant, conventional surfactants can be used, and they include, anionic surfactants such as sodium higher alcohol sulfates, stearyl trimethyl ammonium chloride, polyoxyethylene alkyl phenyl ethers and lauryl betaine; cationic surfactants; nonionic surfactants; amphoteric surfactants; and the like. In addition, a spreader; a wetter-spreader such as dialkyl sulfosuccinates; a binder such as carboxymethyl cellulose and polyvinyl alcohol; a disintegrator such as sodium lignosulfonate, sodium lauryl sulfate and the like can be used.

The amount of the present compound to be contained in the bactericide for agriculture and horticulture as an active ingredient is, for example, 0.01-99.5 mass %, preferably 0.5-90 mass %. The amount may be appropriately determined based on various conditions such as types of formulations, application methods and the like. The bactericide for agriculture and horticulture can be prepared such that it contains an active ingredient in an amount of, for example, about 0.5-20 mass %, preferably 1-10 mass % in the case of a dustable powder, about 1-90 mass %, preferably 10-80 mass % in the case of a wettable powder and about 1-90 mass %, preferably 10-40 mass % in the case of an emulsifiable concentrate.

In the case of an emulsifiable concentrate, for example, an emulsifiable concentrate can be prepared by admixing a solvent and a surfactant with the present compound as an active ingredient, and then the concentrate can be diluted to a predetermined concentration with water upon use to be applied. In the case of a wettable powder, the present compound as an active ingredient, a solid carrier and a surfactant are mixed to give a liquid concentrate, and then the concentrate can be diluted to a predetermined concentration with water upon use to be applied. In the case of a dustable powder, the present compound as an active ingredient, a solid carrier and the like are mixed and the resultant mixture can be applied as it is, and in the case of a granule, the present compound as an active ingredient, a solid carrier, a surfactant and the like are mixed and granulated to give a formulation which can be applied as it is. In this case, however, methods for preparing the above formulations are not limited to those described above and they can be appropriately chosen by those skilled in the art depending on kinds of active ingredients and a purpose for application and the like.

The bactericide for agriculture and horticulture may further contain an optional active ingredient such as another bactericide, an insecticide, a miticide, a herbicide, a plant growth regulator, a fertilizer, a soil conditioner and the like can be admixed in addition to the present compound as an active ingredient. Application methods of the bactericide comprising the present compound are not particularly limited and the application methods which can be employed include, foliage application, soil application, smoking in facilities, stem smoking and the like. For example, in the case of foliage application, a solution at a concentration range, for example, of 5-1000 ppm, preferably of 10-500 ppm can be used in an applied amount of, for example, about 50-700 liters per 10 ares. In the case of soil application, a solution at a concentration range of 5-1000 ppm can be used in an applied amount of about 0.1-1 liter per 1 m².

EXAMPLES

Hereinafter, the present invention will be described in more detail by referring to Examples, Preparation Examples and Test Examples, but the scope of the present invention is not limited by these Examples, Preparation Examples and Test Examples at all.

Example 1

Synthesis of 2-phenoxybenzyl 2-aminonicotinate 0.200 g of 2-phenoxybenzylalcohol, 0.230 g of 1-ethyl-3-(3-dimethylaminopropyl)carbodiimide hydrochloride and 0.146 g of 4-dimethylaminopyridine were added to a solution of 0.138 g of 2-aminonicotinic acid in methylene chloride, and the mixture was heated under reflux for 3 hours. After cooled to room temperature, the mixture was extracted with methylene chloride, and the aqueous layer was further extracted with methylene chloride. The organic layers were combined and dried over anhydrous sodium sulfate. After concentration under reduced pressure, the resulting residue was purified by silica gel column chromatography to yield 0.180 g of Compound No. 1, as an oil, which is described in Table 1 below. In addition, further compounds of the present invention were synthesized in a similar manner. Table 1 below shows the compounds of the present invention which were produced in a similar manner to Example 1.

TABLE 1

[Structure I: pyridine ring with R¹, R², R³, R⁴ substituents, ester linkage to CHR⁴ connected to aromatic ring A with O-linked aromatic ring B bearing R⁵, R⁶; 2-amino group (NH₂) on pyridine]

| Compound No. | R¹ | R² | R³ | R⁴ | A–O–B–R⁵,R⁶ group | mp (° C.) |
|---|---|---|---|---|---|---|
| 1 | H | H | H | H | 2-phenoxyphenyl | Oil¹⁾ |
| 2 | CH₃ | H | H | H | 2-phenoxyphenyl | 129-131 |
| 3 | H | H | H | H | 3-phenoxyphenyl | 102-103 |
| 4 | CH₃ | H | H | H | 3-phenoxyphenyl | 99-100 |
| 5 | H | H | H | H | 4-phenoxyphenyl | 116-118 |

TABLE 1-continued
[I]
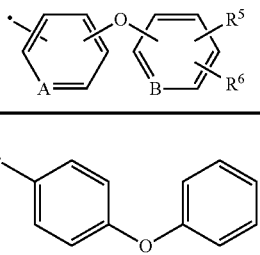
| Compound No. | R¹ | R² | R³ | R⁴ | 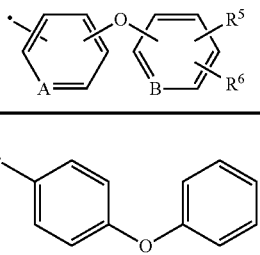 | mp (° C.) |
|---|---|---|---|---|---|---|
| 6 | CH₃ | H | H | H | 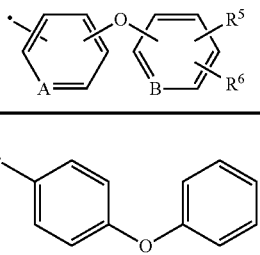 | 107-109 |
| 7 | H | H | H | CH₃ | 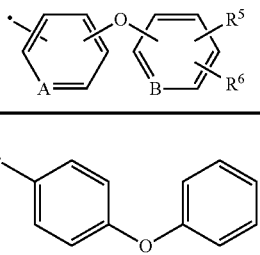 | Oil[2] |
| 8 | CH₃ | H | H | CH₃ | 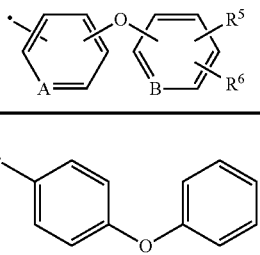 | Oil[3] |
| 9 | H | H | H | CH₃ | 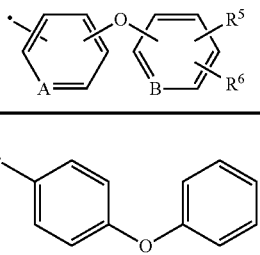 | Oil[4] |
| 10 | CH₃ | H | H | CH₃ | 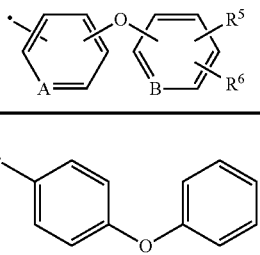 | 96-97 |
| 11 | H | H | H | CN | 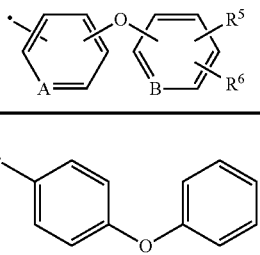 | Oil[5] |
| 12 | CH₃ | H | H | CN | 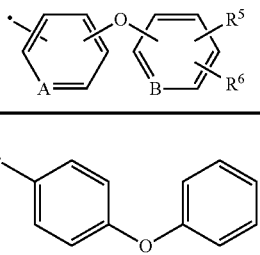 | 146-148 |
| 13 | CH₃ | H | H | H | 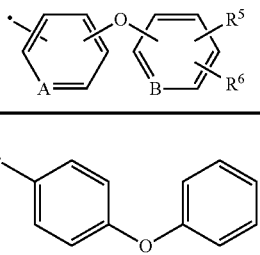 | 94-96 |
| 14 | CH₃ | H | H | H | 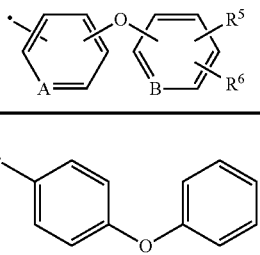 | 107-109 |
| 15 | CH₃ | H | H | H |  | 111-113 |

TABLE 1-continued
[I]
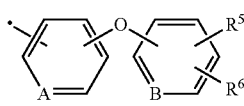
| Compound No. | R¹ | R² | R³ | R⁴ | 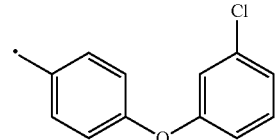 | mp (° C.) |
|---|---|---|---|---|---|---|
| 16 | CH₃ | H | H | H | 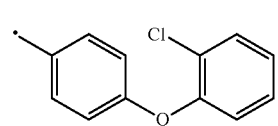 | 85-87 |
| 17 | CH₃ | H | H | H | 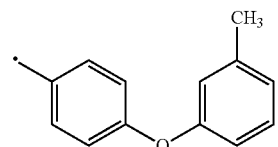 | 115-117 |
| 18 | CH₃ | H | H | H | 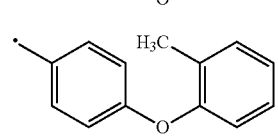 | 106-108 |
| 19 | CH₃ | H | H | H | 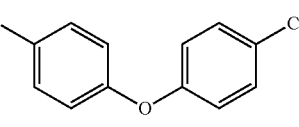 | 89-91 |
| 20 | CH₃ | H | H | H | 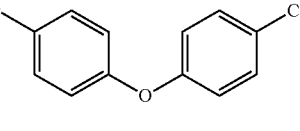 | 114-116 |
| 21 | CH₃ | H | H | H | 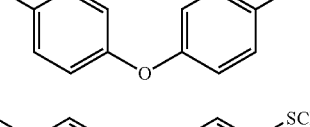 | Oil[6] |
| 22 | CH₃ | H | H | H | 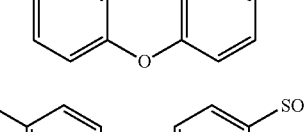 | 129-130 |
| 23 | CH₃ | H | H | H | 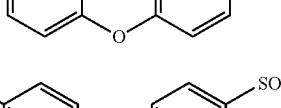 | 161-162 |
| 24 | CH₃ | H | H | H | 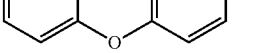 | 166-167 |
| 25 | CH₃ | H | H | H |  | 153-155 |

TABLE 1-continued
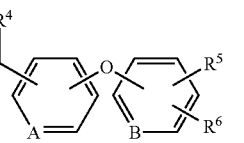
[I]
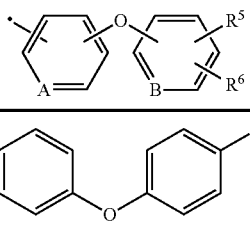
| Compound No. | R¹ | R² | R³ | R⁴ | 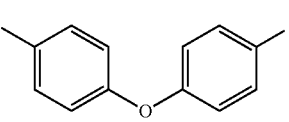 | mp (° C.) |
|---|---|---|---|---|---|---|
| 26 | CH₃ | H | H | H | 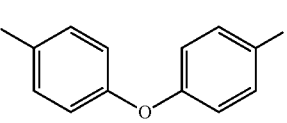 | 106-108 |
| 27 | CH₃ | H | H | H | 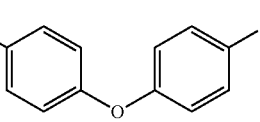 | 104-106 |
| 28 | CH₃ | H | H | H | 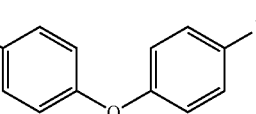 | 133-135 |
| 29 | CH₃ | H | H | H | 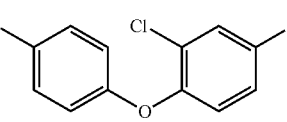 | 136-138 |
| 30 | CH₃ | H | H | H | 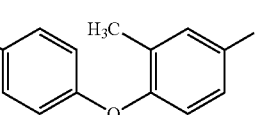 | 118-120 |
| 31 | CH₃ | H | H | H | 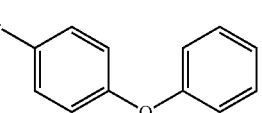 | 143-145 |
| 32 | CH₃ | H | H | H | 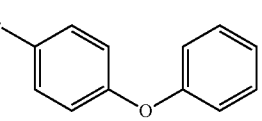 | 122-124 |
| 33 | C₂H₅ | H | H | H | 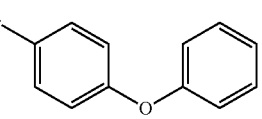 | 111-113 |
| 34 | CH(CH₃)₂ | H | H | H | 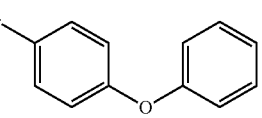 | 73-75 |
| 35 | CH₃ | CH₃ | H | H |  | 123-125 |
| 36 | C₂H₅ | CH₃ | H | H |  | 87-89 |

TABLE 1-continued
[I]
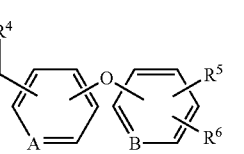
| Compound No. | R¹ | R² | R³ | R⁴ | 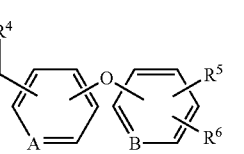 | mp (° C.) |
|---|---|---|---|---|---|---|
| 37 | CH₃ | H | CH₃ | H |  | 126-127 |
| 38 | 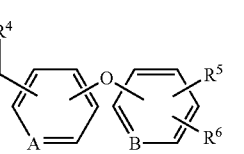 | | H | H |  | 148-150 |
| 39 | 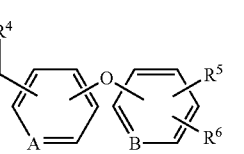 | | H | H | 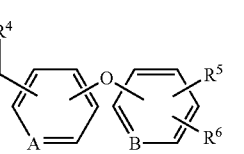 | 121-123 |
| 40 | H | H | H | H | 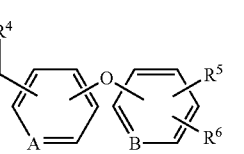 | 117-119 |
| 41 | CH₃ | H | H | H | 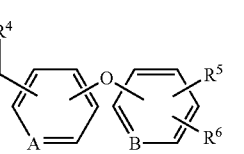 | 106-108 |
| 42 | H | H | H | H | 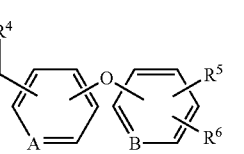 | 83-84 |
| 43 | CH₃ | H | H | H | 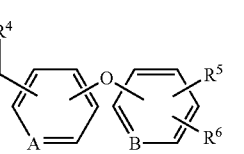 | 120-122 |
| 44 | H | H | H | H | 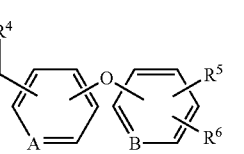 | 134-136 |
| 45 | H | H | H | H | 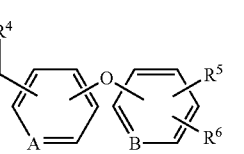 | 118-119 |
| 46 | CH₃ | H | H | H | 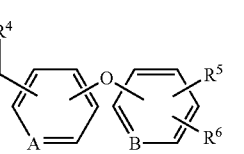 | 120-121 |
| 47 | CH₃ | H | H | H |  | 111-112 |

TABLE 1-continued

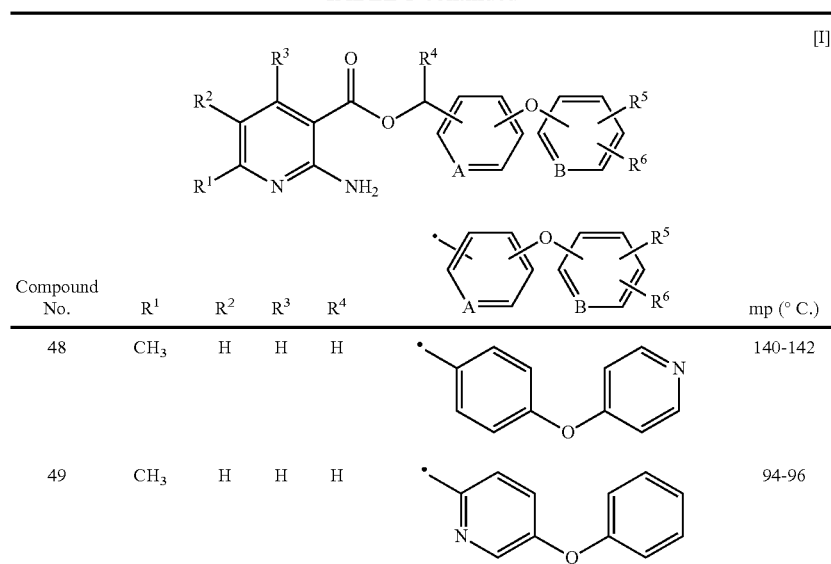

| Compound No. | $R^1$ | $R^2$ | $R^3$ | $R^4$ | ![A-B structure] | mp (° C.) |
|---|---|---|---|---|---|---|
| 48 | $CH_3$ | H | H | H | (4-phenoxy linked to pyridin-4-yl via O) | 140-142 |
| 49 | $CH_3$ | H | H | H | (pyridin-2-yl linked via 5-position-O-phenyl) | 94-96 |

[1] $^1$H-NMR (CDCl$_3$) δ ppm: 4.41 (2H, s), 6.55 (1H, m), 6.93 (3H, m), 7.08 (1H, t), 7.18 (1H, t), 7.28-7.35 (3H, m), 7.52 (1H, d), 7.98 (1H, d), 8.19 (2H. d).
[2] $^1$H-NMR (CDCl$_3$) δ ppm: 1.63 (3H, d), 6.01-6.09 (1H, q), 6.62 (1H, m), 6.91 (1H, d), 7.03 (1H, d), 7.09 (1H, s), 7.11-7.18 (1H, t), 7.29-7.38 (4H, m), 8.19 (1H, d), 8.22 (1H, d)
[3] $^1$H-NMR (CDCl$_3$) δ ppm: 1.64 (3H, d), 2.40 (3H, s), 6.00-6.06 (1H, q), 6.48 (1H, d), 6.92 (1H, d), 7.02 (1H, d), 7.08 (1H, s), 7.09-7.15 (1H, t), 7.30-7.38 (4H, m), 8.06 (1H, d)
[4] $^1$H-NMR (CDCl$_3$) δ ppm: 1.65 (3H, d), 6.07 (1H, q), 6.62 (1H, m), 7.01 (4H, m), 7.12 (1H, t), 7.31-7.41 (4H, m), 8.21 (2H, m).
[5] $^1$H-NMR (CDCl$_3$) δ ppm: 6.47 (1H, s), 6.62 (1H, m), 7.05-7.11 (3H, m), 7.18 (1H, t), 7.22 (1H, s), 7.30-7.45 (4H, m), 8.12 (1H, d), 8.29 (1H, d).
[6] $^1$H-NMR (CDCl$_3$) δ ppm: 2.41 (3H, s), 5.31 (2H, s), 6.48 (1H, q), 7.05 (4H, m), 7.44 (2H, d), 7.59 (2H, d), 8.06 (1H, d)

1) $^1$H-NMR (CDCl$_3$) δ ppm: 4.41 (2H, s), 6.55 (1H, m), 6.93 (3H, m), 7.08 (1H, t), 7.18 (1H, t), 7.28-7.35 (3H, m), 7.52 (1H, d), 7.98 (1H, d), 8.19 (2H. d).

2) $^1$H-NMR (CDCl$_3$) δ ppm: 1.63 (3H, d), 6.01-6.09 (1H, q), 6.62 (1H, m), 6.91 (1H, d), 7.03 (1H, d), 7.09 (1H, s), 7.11-7.18 (1H, t), 7.29-7.38 (4H, m), 8.19 (1H, d), 8.22 (1H, d)

3) $^1$H-NMR (CDCl$_3$) δ ppm: 1.64 (3H, d), 2.40 (3H, s), 6.00-6.06 (1H, q), 6.48 (1H, d), 6.92 (1H, d), 7.02 (1H, d), 7.08 (1H, s), 7.09-7.15 (1H, t), 7.30-7.38 (4H, m), 8.06 (1H, d)

4) $^1$H-NMR (CDCl$_3$) δ ppm: 1.65 (3H, d), 6.07 (1H, q), 6.62 (1H, m), 7.01 (4H, m), 7.12 (1H, t), 7.31-7.41 (4H, m), 8.21 (2H, m).

5) $^1$H-NMR (CDCl$_3$) δ ppm: 6.47 (1H, s), 6.62 (1H, m), 7.05-7.11 (3H, m), 7.18 (1H, t), 7.22 (1H, s), 7.30-7.45 (4H, m), 8.12 (1H, d), 8.29 (1H, d).

6) $^1$H-NMR (CDCl$_3$) δ ppm: 2.41 (3H, s), 5.31 (2H, s), 6.48 (1H, q), 7.05 (4H, m), 7.44 (2H, d), 7.59 (2H, d), 8.06 (1H, d)

Next, Preparation Examples will be shown. In the Preparation Examples, parts represent parts by mass.

Preparation Example 1

Emulsifiable Concentrate

A compound of the present invention (10 parts), xylene (60 parts), N-methyl-2-pyrrolidone (20 parts) and Sorpol 3005X (a mixture of a nonionic surfactant and an anionic surfactant, TOHO Chemical Industry Co., Ltd., Japan, a trade name) (10 parts) were mixed and dissolved uniformly to give an emulsufible concentrate.

Preparation Example 2

Wettable Powder—1

The compound of the present invention (20 parts), Nipsil NS-K (white carbon, Tosoh Silica Corporation, Japan, a trade name) (20 parts), Kaolin Clay (kaolinite, TAKEHARA KAGAKU KOGYO CO., LTD., Japan, a trade name) (70 parts), Sanx P-252 (sodium lignosulfonate, NIPPON PAPER INDUSTRIES CHEMICAL Div., Japan, a trade name) (5 parts) and Runox P-65L (an alkylarylsulfonate, TOHO Chemical Industry Co., Ltd., Japan, a trade name) (5 parts) were mixed and ground uniformly by means of an air mill to give a wettable powder.

Preparation Example 3

Wettable Powder—2

The compound of the present invention (20 parts), Nipsil NS-K (20 parts), Kaolin Clay (50 parts), Runox 1000C (a salt of naphthalenesulfonic acid condensate, TOHO Chemical Industry Co., Ltd., Japan, a trade name) (5 parts) and Sorpol 5276 (a nonionic surfactant, TOHO Chemical Industry Co., Ltd., Japan, a trade name) (5 parts) were mixed and ground uniformly by means of an air mill to give a wettable powder.

Preparation Example 4

Suspension Concentrate (Flowable)—1

The compound of the present invention (20 parts) was dispersed in a previously mixed mixture of propylene glycol (5 parts), Sorpol 7933 (an anionic surfactant, TOHO Chemical Industry Co., Ltd., Japan, a trade name) (5 parts) and water (50 parts) to make a slurry mixture, and then the slurry mixture was wet ground by means of a Dyno-Mill (Shinmaru Enterprises Corporation, Japan), and to the resulting material, a well premixed dispersion of xanthan gum (0.2 part) in water (19.8 parts) was added to give a suspension concentrate (flowable).

Preparation Example 5

Suspension Concentrate (Flowable)—2

A compound of the present invention (20 parts), Newkalgen FS-26 (a mixture of dioctyl sulfosuccinate and polyoxyethylene tristyryl phenyl ether, TAKEMOTO OIL & FAT Co. Ltd., Japan, a trade name) (5 parts), propylene glycol (8 parts) and water (50 parts) were premixed to give a slurry mixture and then the slurry mixture was wet ground by means of a Dyno-Mill (Shinmaru Enterprises Corporation, Japan). Then, xanthan gum (0.2 part) was well mixed and dispersed into water (16.8 parts) to give a gelatinous material, and the gelatinous material was sufficiently mixed with the ground slurry to give a suspension concentrate (flowable).

Then, the following Test Examples will prove that the present compounds are useful as an active ingredient of a bactericide. In Test Examples, the present compounds used are shown by their Compound Numbers described on Table 1, and a compound used as a comparative control is shown by the following compound (a compound described in Examples of Patent Document 1).

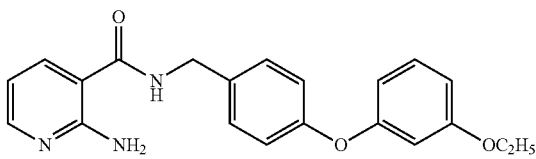

Compound A (Patent Document 1)

Test Example 1

A Test on *Botrytis cinerea* (Gray Mold) of a Cucumber

A cucumber plant (a plant variety: "Sagami Han-shiro") of 12 days after seeding was prepared for the test. Parts of cotyledons of the cucumber plant were cut out with leaving about 2 cm of its rachis. Apart from this, a plastic case with a size of 32 cm×24 cm×4.5 cm (length×width×height), at the bottom of which a paper towel sufficiently moistened with water was laid, and on the paper towel a mesh with legs was placed, was prepared. On the mesh, the above-described cutout parts of cotyledons were placed such that leaves were horizontal. To the central part of each of the cotyledons, 50 μl of a spore suspension (1×10$^6$ spores/ml) of *Botrytis cinerea* of a cucumber was added dropwise. Thereafter, each of cotyledons was covered with a paper disc with a diameter of 6 mm. Apart from this, an emulsion prepared according to the above Preparation Example 1 was diluted with an aqueous solution of 0.02% Tween 20 in demineralized water to prepare a diluent of a predetermined concentration. 50 μl of the diluent was dropped on each paper disc. The plastic case was lidded and was placed under the condition of 20° C. for 72 hours, and then the diameter of each lesion was measured and the controlling rate for *Botrytis cinerea* (gray mold) of a cucumber was calculated according to the following equation. The results are shown in Table 1.

Controlling rate (%)=[1−(diameter of lesion in treatment region/diameter of lesion in non-treatment region)]×100

Table 2

| *Botrytis cinerea* (gray mold) of a cucumber | | |
|---|---|---|
| Compound No. | Conc. (ppm) | Controlling rate (%) |
| 5 | 25 | 100 |
| 6 | 25 | 100 |
| 13 | 25 | 100 |
| 14 | 25 | 100 |
| 15 | 25 | 100 |
| 17 | 25 | 100 |
| 18 | 25 | 100 |
| 19 | 25 | 100 |
| 20 | 25 | 100 |
| 27 | 25 | 100 |
| 34 | 25 | 100 |
| 35 | 25 | 100 |
| 36 | 25 | 100 |
| 40 | 25 | 100 |
| 41 | 25 | 100 |
| 43 | 25 | 100 |
| 46 | 25 | 100 |
| 47 | 25 | 100 |
| 49 | 25 | 100 |
| A | 25 | 54 |

As shown in Table 2 above, the present compounds exhibit a higher bactericidal activity as compared with that of the compound A.

The invention claimed is:

1. A 2-aminonicotinic acid ester compound represented by the following formula [I]:

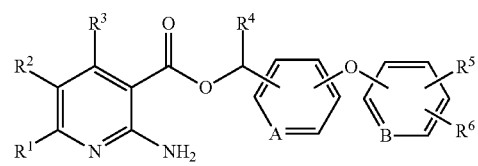

wherein:
$R^1$ represents a hydrogen atom or a $C_1$-$C_4$ alkyl group,
$R^2$ represents a hydrogen atom, a $C_1$-$C_4$ alkyl group, or $R^1$ and $R^2$ are combined together to form:

or

, $R^3$ represents a hydrogen atom or a $C_1$-$C_4$ alkyl group,
$R^4$ represents a hydrogen atom, a cyano group or a $C_1$-$C_4$ alkyl group,
$R^5$ and $R^6$ independently represent a hydrogen atom, a halogen, a $C_1$-$C_4$ alkyl group, a $C_1$-$C_4$ alkoxy group, a $C_1$-$C_4$ alkylthio group, a $C_1$-$C_4$ alkylsulfinyl group, a $C_1$-$C_4$ alkylsulfonyl group, a nitro group, a cyano group, a $C_1$-$C_4$ haloalkyl group, a $C_1$-$C_4$ haloalkoxy group or a $C_1$-$C_4$ haloalkylthio group,
A and B independently represent a methine (CH) group or a nitrogen atom.

2. A bactericide comprising the 2-aminonicotinic acid ester compound according to claim 1 as an active ingredient.

\* \* \* \* \*